United States Patent
Phinney et al.

(10) Patent No.: US 6,407,599 B1
(45) Date of Patent: Jun. 18, 2002

(54) METHOD AND APPARATUS FOR DETERMINING A DIGITAL PHASE SHIFT IN A SIGNAL

(75) Inventors: Daniel P. Phinney; David M. Pultorak, both of Rochester, NY (US)

(73) Assignee: Eastman Kodak Company, Rochester, NY (US)

(*) Notice: Subject to any disclaimer, the term of this patent is extended or adjusted under 35 U.S.C. 154(b) by 0 days.

(21) Appl. No.: 09/567,896

(22) Filed: May 10, 2000

(51) Int. Cl.⁷ .................................................. H03L 7/00
(52) U.S. Cl. ........................ 327/151; 327/241; 327/244
(58) Field of Search ................................. 327/2, 3, 7, 9, 327/24, 33, 244, 142, 151, 160, 163, 236, 241

(56) References Cited

U.S. PATENT DOCUMENTS

| | | |
|---|---|---|
| 3,663,956 A | 5/1972 | Purdy et al. |
| 3,813,165 A * | 5/1974 | Hines et al. ................ 356/5.12 |
| 3,953,794 A | 4/1976 | Moore |
| 4,066,969 A | 1/1978 | Pearce et al. |
| 4,370,574 A | 1/1983 | Nielsen |
| 4,400,664 A | 8/1983 | Moore |
| 4,408,165 A | 10/1983 | Braun |
| 4,425,543 A | 1/1984 | Adams et al. |
| 4,600,994 A | 7/1986 | Hayashi |
| 4,607,218 A | 8/1986 | Stosel |
| 4,775,890 A | 10/1988 | Balaban et al. |
| 4,963,817 A | 10/1990 | Kohiyama et al. |
| 5,151,638 A | 9/1992 | Beckerman |
| 5,266,851 A | 11/1993 | Nukui |
| 5,432,826 A | 7/1995 | Rieder |
| 5,438,254 A | 8/1995 | Ho et al. |
| 5,481,198 A | 1/1996 | Patel |
| 5,506,874 A | 4/1996 | Izzard et al. |
| 5,568,071 A | 10/1996 | Hoshino et al. |
| 5,583,458 A | 12/1996 | Bazes |
| 5,619,148 A | 4/1997 | Guo |
| 5,818,265 A | 10/1998 | Meller et al. |
| 5,903,605 A | 5/1999 | Crittenden |
| 5,949,260 A | 9/1999 | Toda |

* cited by examiner

*Primary Examiner*—Kenneth B. Wells
*Assistant Examiner*—Cassandra Cox
(74) *Attorney, Agent, or Firm*—Nelson Adrian Blish

(57) ABSTRACT

A method for determining a digital phase in a signal comprises sampling a reference signal for a low going edge. If the low going edge is not detected the reference signal is sampled again. If low going edge is detected (78) a counter is initialized (70). The reference signal is again sampled if a high going edge is not detected the reference signal is resampled until the high going edge is detected (79). When a high going edge is detected (79) a counter is started (73). A resulting signal is then sampled if the level of the resulting signal is high the resulting signal is sampled until a low going edge is detected (78). If a low going edge is not detected sampling of the resulting signal continues. If a low going edge is detected (78) sampling is continued until a high going edge is detected (79) at which point the counter is stopped (76). The counter updates a register (96). When the resulting signal was sampled for a high level the resulting signal is sampled until a high going edge is determined (79) at which point the register is stopped and converted to a phase difference (84). In one embodiment of the invention the reference signal being sampled is a driver for an ultrasonic transmitter (14) and the resulting signal is an electrical signal (21) representative of a received ultrasonic signal (16).

21 Claims, 8 Drawing Sheets

METHOD AND APPARATUS FOR DETERMINING A DIGITAL PHASE SHIFT IN A SIGNAL

FIELD OF THE INVENTION

This invention relates in general to detectors for multiple document feeds and in particular to detecting a phase shift in an ultrasonic signal.

BACKGROUND OF THE INVENTION

Scanners and copiers use document feeders to transport documents into the machine. Mechanisms used for the transportation of documents, including paper or sheets of other material, have the capacity to accidentally pick up more than one document fed from a stack of documents. It is necessary to determine when more than one document is pulled into a document transport since multiple documents may jam the transport or prevent processing some documents.

There are two general methods for multiple document detection, contact and non-contact. The contact methods include measurement of small thickness changes with a contact foot or sensing arm that is in contact with the documents as they pass through the document transport. The contact foot is connected to a Linear Voltage Differential Transducer (LVDT), or a magnet, which is sensed by a Hall Effect Sensor. These sensors can detect changes in thickness of less than 1 μm ($10^{-6}$ m).

The major disadvantage to the contact method is that anything in contact with moving paper, especially thin paper or ripped paper, can cause a malfunction such as a paper jam. The contact method also requires calibration using the maximum thickness document that will be fed through the document transport. When a thickness is measured which is above the calibration value plus a threshold, typically 30%, it is determined to be a multiple document feed. This method, however, will only work when documents having a uniform thickness are processed. Using a wheel on the end of the contact foot can reduce the chances of paper jam, however, the variations in the diameter of this wheel, due to the nonconformity in manufacturing, must be taken into account during the measurements.

The primary non-contact method for multiple document detection sends ultrasound signals through the document stream to determine if more than one document is present. Sending ultrasound through paper results in attenuation of the ultrasound signal. It is possible to determine the presence of multiple documents by change in attenuation of the signal received. This method is independent of the thickness of the individual documents and is made without making contact with these documents.

A typical contact document scanner is able to detect about 94% of the test multiple documents. An attenuation detector that was tested was only able to detect about 86% of these same test multiple documents, thus there is an opportunity for improvement using ultrasound detection.

For detecting multiple documents by attenuation methods, the performance improves as higher frequency transmitters and receivers are used. Unfortunately, the cost of these components also increases with frequency. There is also a limited range of paper thicknesses that can be properly detected. Therefore, the attenuation method alone is not suitable for multiple document detection.

The phase shift of ultrasound signal passing through documents has been used to detect multiple document feeds. See U.S. Pat. No. 4,066,969 which is herein incorporated by reference. Unfortunately, using phase shift is not reliable since multiple documents may cause phase shifts greater than 360 degrees. For detecting multiple documents by phase methods, the performance decreases at higher frequencies because the wavelength is shorter and the method becomes more sensitive to signal variations.

SUMMARY OF THE INVENTION

The present invention provides an improved method and apparatus for multiple document detection, which is both accurate and relatively inexpensive.

According to one aspect of the present invention a method for determining a digital phase in a signal comprises sampling a reference signal for a low going edge. If the low going edge is not detected the reference signal is sampled again. If low going edge is detected a counter is initialized. The reference signal is again sampled if a high going edge is not detected the reference signal is resampled until the high going edge is detected. When a high going edge is detected a counter is started. A resulting signal is then sampled if the level of the resulting signal is high the resulting signal is sampled until a low going edge is detected. If a low going edge is not detected sampling of the resulting signal continues. If a low going edge is detected sampling is continued until a high going edge is detected at which point the counter is stopped. The counter updates a register. When the resulting signal was sampled for a high level the resulting signal is sampled until a high going edge is determined at which point the register is stopped and converted to a phase difference. In one embodiment of the invention the reference signal being sampled is a driver for an ultrasonic transmitter and the resulting signal is an electrical signal representative of a received ultrasonic signal.

A method for determining a phase shift in a signal which is transmitted and received in accordance with another embodiment of the present invention requires a few steps. In this method, a counter is started when a first cross over location from a first-state-to-second-state is detected in the transmitted signal. The counter is stopped when a second cross over location in the received signal is detected which matches the first-state-to-second-state direction of the first cross over location in the transmitted signal. A counter value in the counter is then converted to obtain a phase difference between the transmitted and received signal.

A method for determining the presence of multiple documents in accordance with yet another embodiment of the present invention also requires a few steps. In this method, a signal is transmitted through a document feed comprising one or more documents. The signal is received after it has passed through the document feed. A counter is started when a first cross over location from a first-state-to-second-state is detected in the transmitted signal. The counter is stopped when a second cross over location in the received signal is detected which matches the first-state-to-second-state direction of the first cross over location in the transmitted signal. A counter value in the counter is converted to a phase difference which identifies the number of the documents in the document feed.

An apparatus for determining a phase shift in accordance with another embodiment of the present invention includes a signaling system which transmits and receives a signal, a counter, a detector, and a converter. The detector starts the counter when a first cross over location from a first-state-to-second-state is detected in the transmitted signal and stops the counter when a second cross over location in the received signal is detected which matches the first-state-to-second-state direction of the first cross over location in the transmitted signal. The converter converts a counter value in the counter to a phase difference between the transmitted and received signals.

An apparatus in accordance with yet another embodiment of the present invention includes a document processing system, a document transport system, a signaling system which transmits and receives a signal, a counter, a detector, and a converter. The document transport system supplies at least one document feed to the document processing system and the document feed comprises one or more documents. The detector starts the counter when a first cross over location from a first-state-to-second-state is detected in the transmitted signal and stops the counter when a second cross over location in the received signal is detected which matches the first-state-to-second-state direction of the first cross over location in the transmitted signal. The converter converts a counter value in the counter to a phase difference which identifies the number of the documents in the document feed.

An advantage of the present invention is that detection device makes no contact with the paper and is relatively independent of the paper thickness.

Another advantage of the present invention is that it will cause less document jams than direct contact methods.

Yet other advantages of this invention are: lower cost than traditional phase difference measurements methods; reduced susceptibility to noise as compared to traditional methods; and more accuracy and repeatability.

DETAILED DESCRIPTION OF THE INVENTION

Figure 4A:
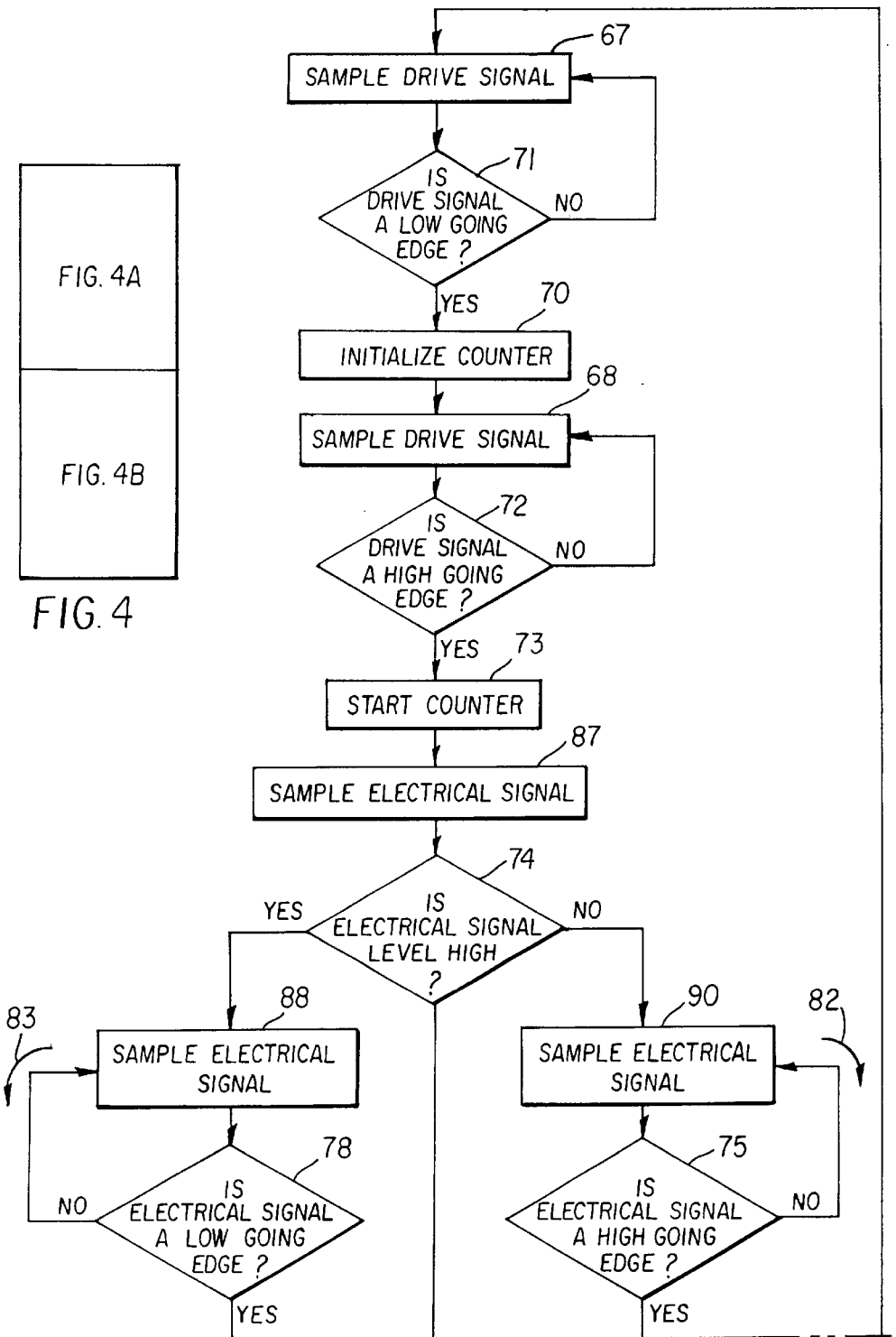
FIG. 4 is a flow chart for phase shift detection for the state diagram shown in FIG. 3.
Figure 4B:
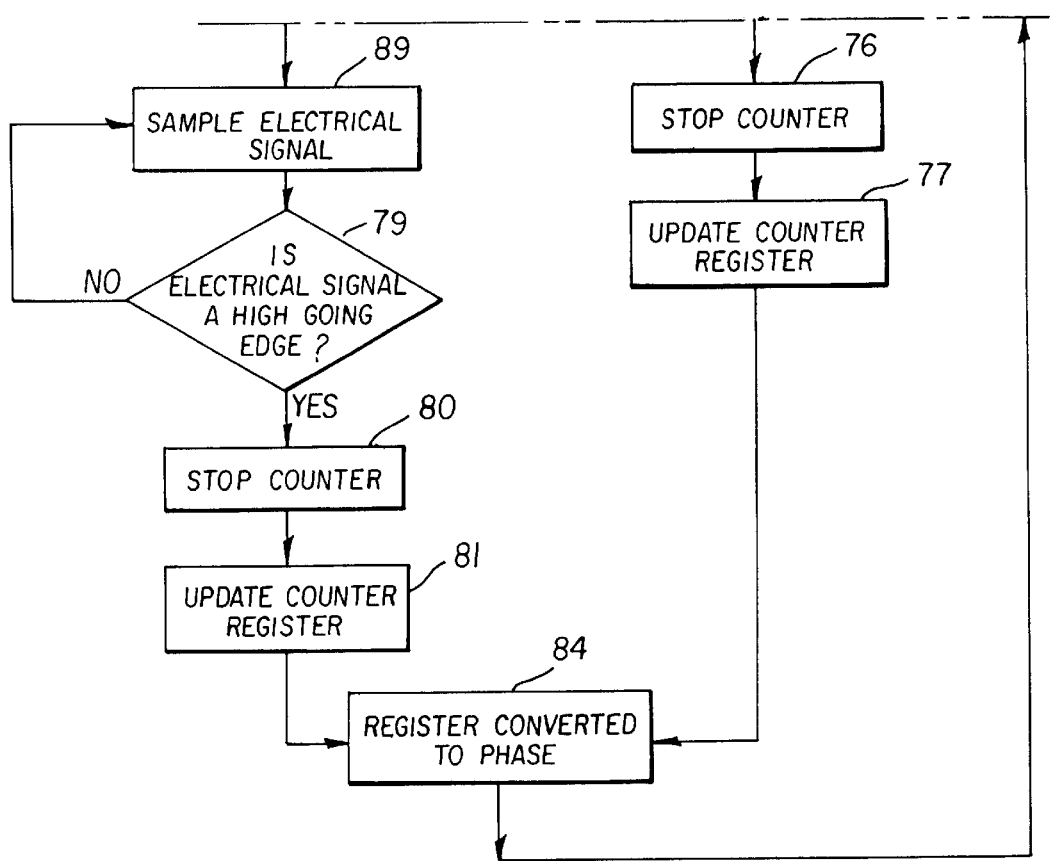

A method for determining a phase shift in a signal which is transmitted and then received in accordance with one embodiment of the present invention is illustrated in FIG. 4. This method involves starting a counter when a first cross over location from a first-state-to-second-state is detected in the transmitted signal and then stopping the counter when a second cross over location in the received signal is detected which matches the first-state-to-second-state direction of the first cross over location in the transmitted signal. A counter value in the counter is then converted to obtain a phase difference between the transmitted and received signal. The present invention provides a number of advantages including providing a simpler and more accurate method for determining the phase difference between two signals, providing a method and system which does not require any analog processing, and providing a less expensive system for determining the phase difference between two signals.

Figure 1:
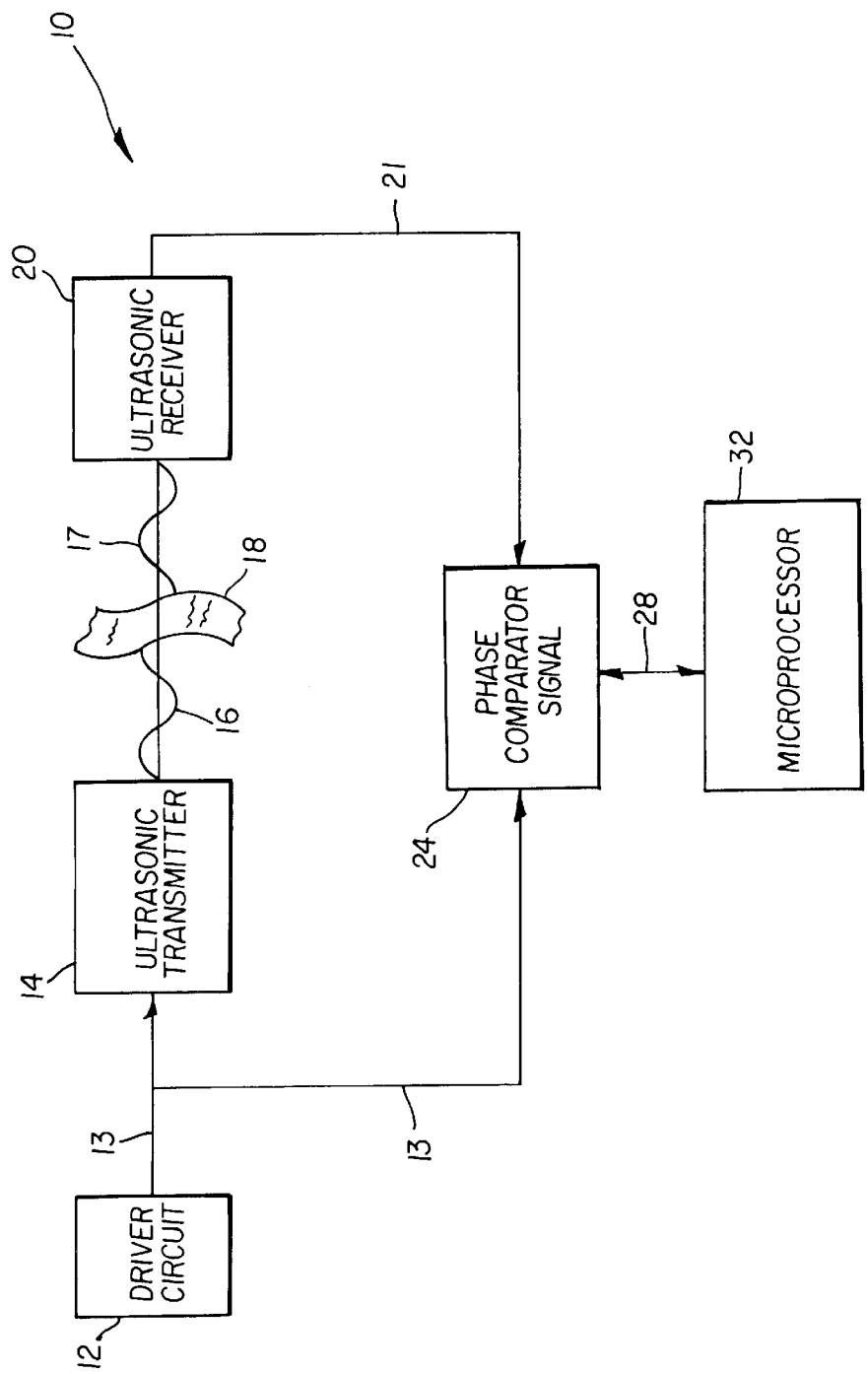
FIG. 1 is a block diagram of detection circuit using phase shift measurement in accordance with one embodiment of the present invention.

Referring to FIG. 1, an apparatus 10 for multiple document detection in accordance with one embodiment of the present invention is shown. In this particular embodiment, the apparatus 10 includes an ultrasonic drive circuit 12 which provides a drive signal 13 to an ultrasonic transmitter 14. The ultrasonic transmitter 14 produces an ultrasonic signal 16 that passes through a document feed 18 which comprises one or more documents and is received by an ultrasonic receiver 20. A phase shift of the ultrasonic signal 16 is relatively independent of the thickness of the document or documents in the document feed 18. This results in a received ultrasonic signal 17 with a phase shift approximately dependent on only the number of documents in the document feed 18, because of the interfaces between different materials through which the ultrasound passes causes the phase shift, not the total thickness of the documents.

The ultrasonic receiver 20 converts the received ultrasonic signal 17 into an electrical signal 21. The electronic signal 21 is supplied to an input to a phase comparator 24 where the phase difference between the drive signal 13 and the electronic signal 21 is determined as explained in greater detail below with references to FIGS. 3–5. An information signal 28 which represents the determined phase difference is fed from phase comparator 24 to a microprocessor 32. The microprocessor 32 monitors information signal 28 to determine if multiple documents are present based on the resulting phase shift or difference between the drive signal 13 and the electronic signal 21. Although a microprocessor 32 is shown, other types of processors or programmable devices can also be used. Additionally although in this particular example, an ultrasonic signal is used in this apparatus 10, other types of signals, such as electromagnetic, can also be used.

Figure 2:
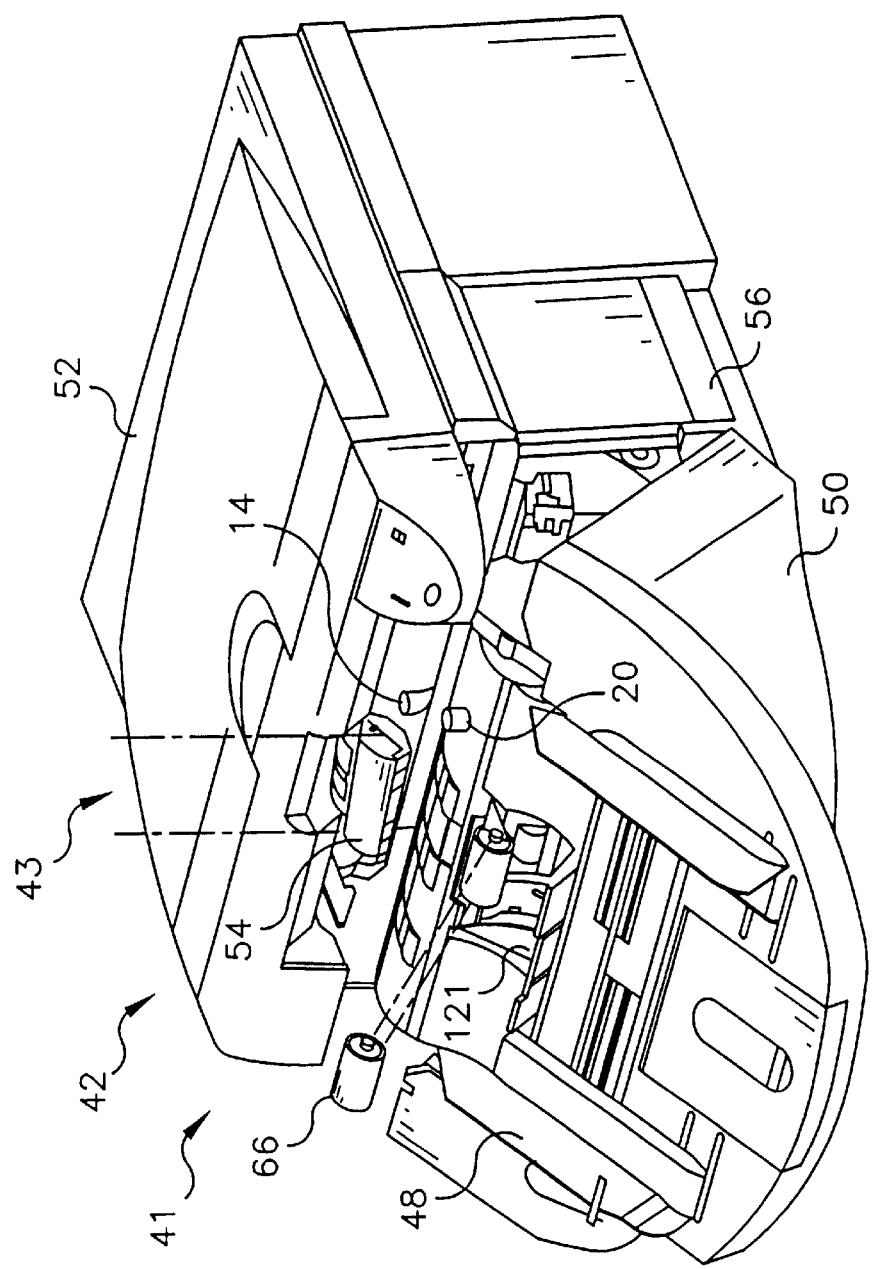
FIG. 2 is a perspective view of a typical sheet feeding device.

Referring to FIG. 2, a typical device employing a document transport, in this case a sheet feeder, is shown. In this particular embodiment, the sheet feeding device 42 comprises a stack support 48 disposed in a first portion 50 of a housing 52. A feed module 54 is detachably mounted in a second portion 56 of the housing 52 so as to be in contact with a stack of documents. Separator 66 is a mechanical device for reducing multiple feeds. Ultrasonic transmitter 14 and ultrasonic receiver 20 are positioned so that documents are transported between them after the documents leave the stack. Other locations in the document transport system may also be suitable for positioning the ultrasonic transmitter 14 and receiver 20. Multiple documents which are not physically separated by separator 66 are detected as described above herein.

The present invention provides a digital method to obtain a phase difference measurement without the need for any analog processing. The phase difference between two signals can be determined digitally by measuring the time difference of the zero or other set level crossover point or location of these two signals. Alternately, the phase difference can be determined from the time differences of the high going or low going edges of these two signals.

Figure 3:
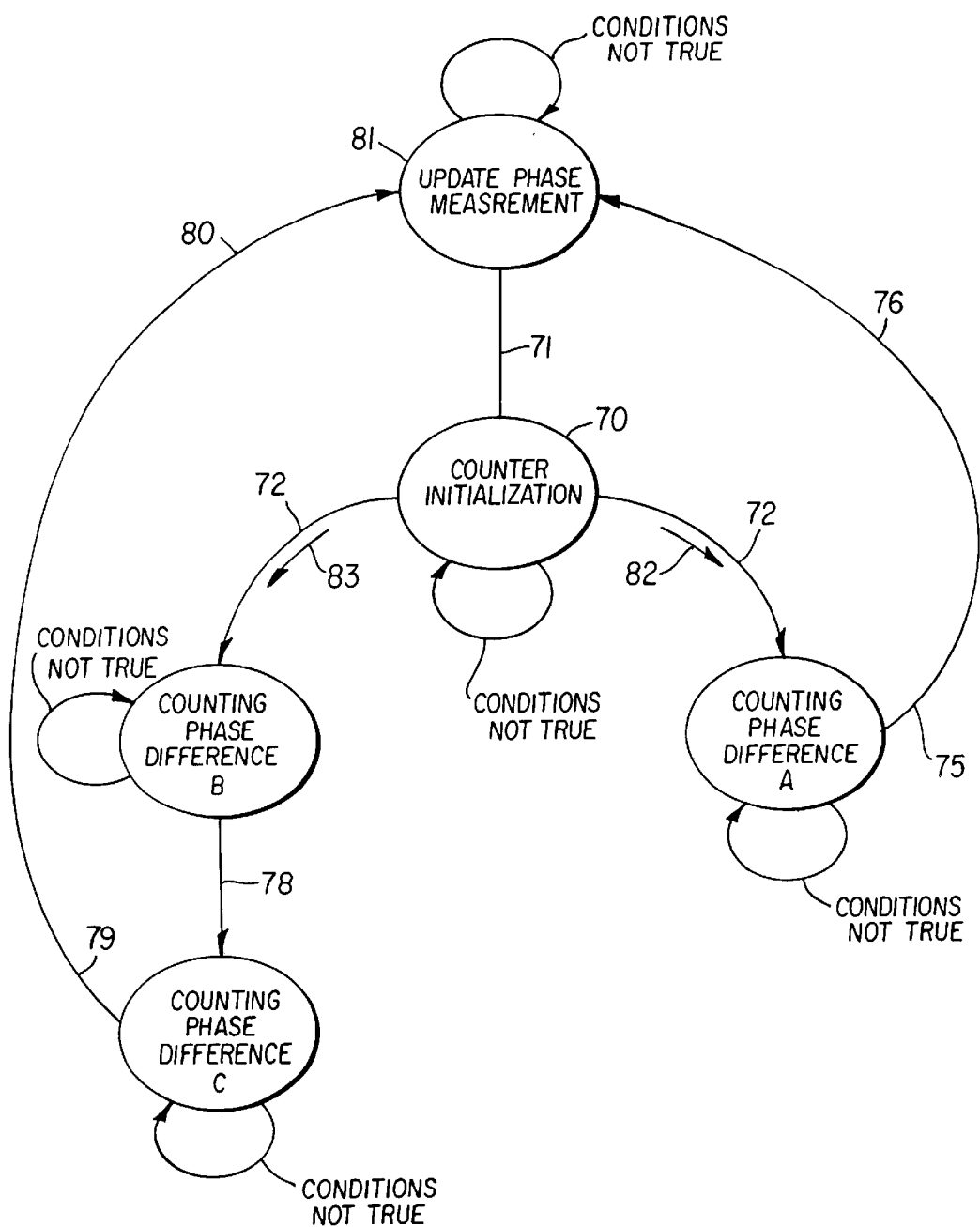
FIG. 3 is state diagram of an algorithm used for determination of phase shift according to one embodiment of the present invention.
Figure 5:
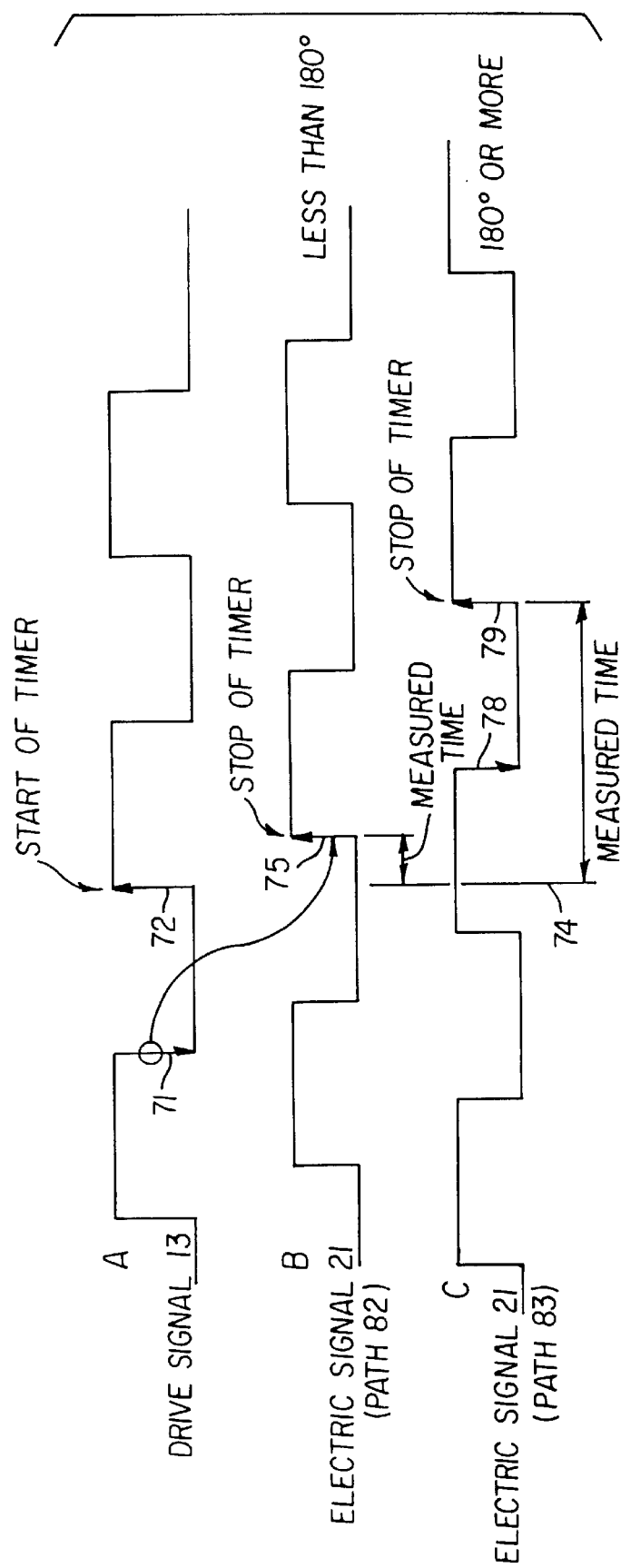
FIG. 5 are wave forms showing a phase shift.

Referring to FIGS. 3–5, a method in accordance with one embodiment of the present invention is illustrated. In this particular embodiment, the drive signal 13 is used as a reference signal and is sampled 67. If a low going level is detected 71 the counter is initialized 70. If a lower going edge is not detected the drive signal is sampled again 67.

After the counter is initialized, the drive signal is sampled again 68. If a high going edge is not detected the drive signal 13 is resampled 68. When a high going edge is detected 72 the counter is started 73.

The electrical signal 21 is sampled 87. If the electrical signal level is at a high level, path 83 is selected and the electrical signal 21 is sampled 88. If a low going edge is not detected 78, sampling continues 88. When low going edge is detected 78 sampling of the electrical signal 21 continues 89.

The reason for detecting a low going edge is shown by reference to wave form A and wave form C in FIG. 5. Since the level of the electric signal is high there is the possibility that the high going edge of the electric signal 21 and the drive signal 13 could coincide so the first low going edge must be detected, which is shown schematically by the total measured time. Thus, phase differences greater than one half cycle may be measured.

Sampling of the electrical signal 21 continues at step 89 until a high going edge is detected 79. At this point the counter is stopped 80 and the counter register value is updated 81. If a high going edge is not detected the electrical signal 21 is resampled 89. The counter register 81 is converted to an actual phase value 84 by a microprocessor and the drive signal is again sampled 67 for a low going edge.

If the electrical level is not high 74, path 82 is selected and the electrical signal is sampled 90 for a high going edge. When a high going edge is detected 75 the counter is stopped 76 and the counter register is updated 77. If a high going edge is not detected 75 the electrical signal is resampled 90. When the counter register is updated 77 it is converted to a phase value 84 by the microprocessor and the drive signal is again monitored for a low going edge 67.

In summary, if the electrical signal 21 is low, the phase difference is represented by the time until the electrical signal 21 goes high. If the electrical signal 21 is high when the drive signal 13 goes high, the phase difference is represented by the time until the electrical signal 21 goes low and then high again. The algorithm shown by the state diagram in FIG. 3 will handle the situation where the electrical signal 21 is either leading or lagging the drive signal 13 by 180 degrees or less. Although in this particular embodiment, triggering events comprise detected low going and high going edges as described above, it would be readily apparent to one of ordinary skill in the art that other triggering events could also be used, such as switching all of the triggering events for low going edges to high going edges and all of the triggering events for high going edges to low going edges.

Figure 7:
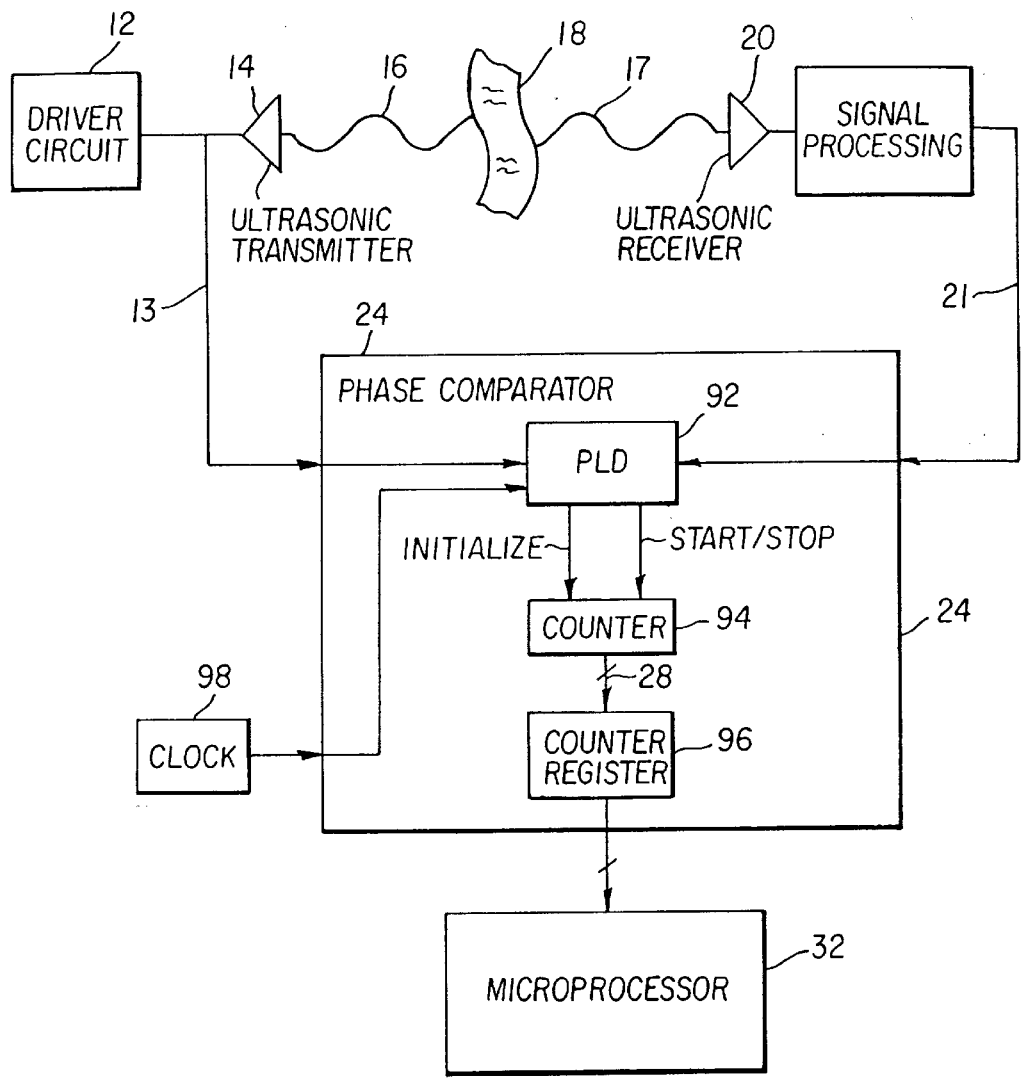
FIG. 7 is a block diagram of detection circuit including a detailed block diagram of the phase comparator circuit in accordance with another embodiment of the present invention.

In this particular embodiment, the sample rate is controlled by a clock 98 shown in FIG. 7. Using a faster clock will increase the sample rate and hence the resolution and accuracy. The counter measures the number of clock pulses. Since a digital value of the time difference is obtained by reference to the counter, this value can be input directly into a microprocessor 32 or any digital logic unit for easy processing. This method will provide a full 360 degrees of phase shift measurement before phase wrap around occurs.

Figure 6:
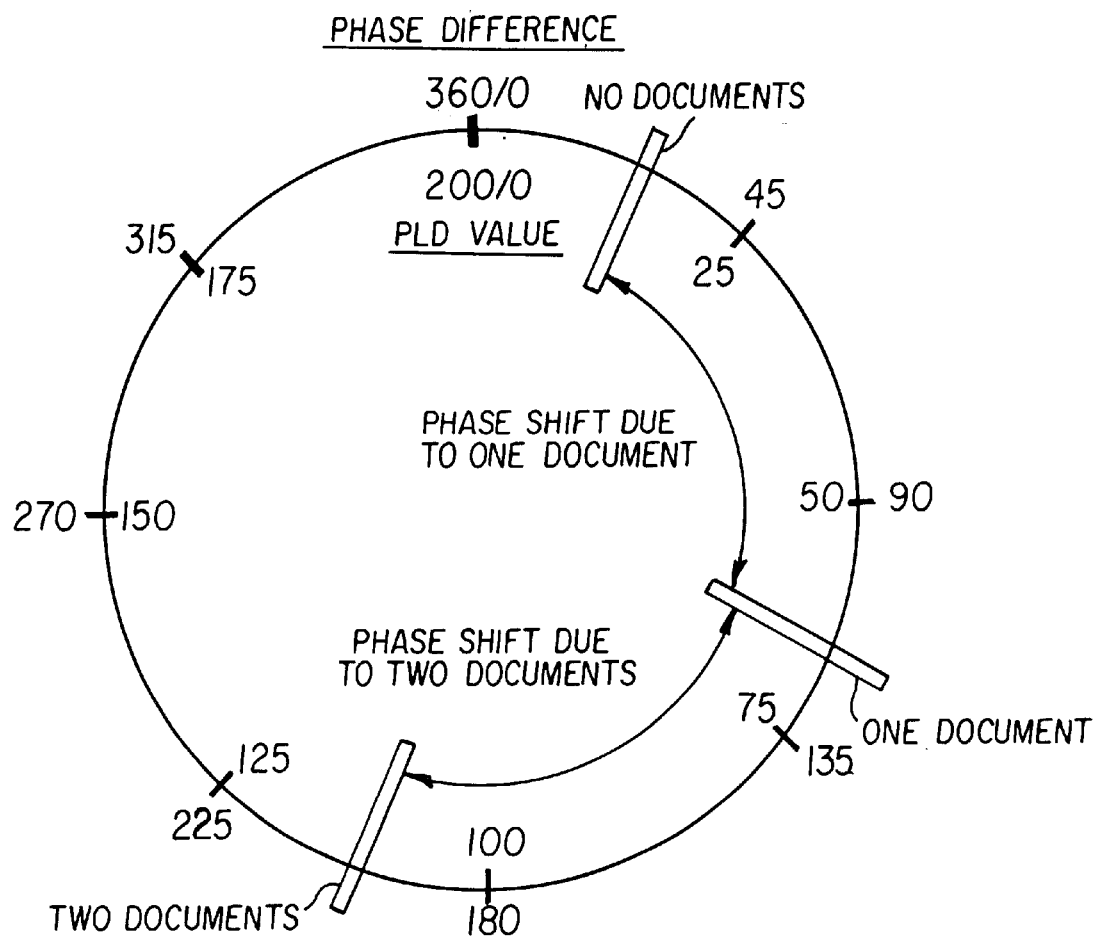
FIG. 6 is a schematic diagram of a phase shift between a driver signal and an electrical signal.

As applied to detection of multiple documents, the phase shift indicates the presence of more than one document. Referring now to FIG. 6 essentially no phase shift will occur when no documents are present. The presence of one document causes a phase shift of approximately 90 degrees. If two documents are present the phase shift will be approximately 180 degrees with some margin of error. A number of factors cause variation in the exact phase difference for two documents, some of which include thickness of the documents, angle of the transmitter and receiver, and angle of the document within the ultrasound path. This invention provides a method of obtaining reliable and inexpensive measurement of the presence of multiple documents, wherein the phase shift may exceed 180 degrees.

FIG. 7 shows additional details of the phase comparator 24 in accordance with another embodiment of the present invention. In this particular embodiment, the programmable logic device (PLD) 92 incorporates the algorithm shown in FIG. 3. The PLD starts and stops counter 94 according to the criteria described above with reference to FIG. 4. The counter values are transferred to the counter register 96 at the completion of a phase measurement cycle. Microprocessor 32 periodically samples counter register 96. The rate of sampling by the microprocessor 32 may be set at different values however, for example, a low volume document transport system may sample 2000 times per second. Clock 98 provides a sample rate signal to counter 94 and PLD 92. Clock rate 98 may sample at a rate of 32 $\mu$sec although other clock rates are available as described above. As the above-described method and system illustrate, the phase shift difference between the drive signal 13 and the electrical signal 21 can be obtained without any analog processing, using only digital methods. As a result, the present invention is simpler and can be implemented less expensively and with greater precision than prior analog systems for measuring phase shift differences between signals.

The invention has been described in detail with particular reference to certain preferred embodiments thereof, but it will be understood that variations and modifications can be effected within the scope of the invention. For example, although the invention has been described as applied to a system for detecting phase shift in an ultrasonic application, the invention can be applied more broadly to any system for detection of changes in the phase of signals. In the broader sense the drive signal can be any reference signal and the electrical signal will be the resulting signal after some perturbation causing a phase shift.

PARTS LIST

10. Apparatus
12. Ultrasonic drive circuit
13. Drive signal
14. Ultrasonic transmitter
16. Ultrasonic signal
17. Ultrasonic signal
18. Document feed
20. Ultrasonic receiver
21. Electrical signal
24. Phase comparator
28. Information signal
32. Microprocessor
42. Sheet feeding device
48. Stack support
50. First portion
52. Housing
54. Feed module
56. Second portion
66. Separator
67. Sample drive signal
68. Sample drive signal
70. Counter initialized
71. Low going level detected 72. High going edge determined
73. Counter started
74. Electrical level not high
75. High going edge detected
76. Counter stopped
77. Counter register updated
78. Low going edge detected
79. High going edge detected
80. Counter stopped
81. Counter register value updated
82. Path less than 180 degrees phase difference
83. Path more than 180 degrees phase difference
84. Convert actual phase value
87. Sample electrical signal
88. Sample electrical signal
89. Sample electrical signal
90. Sample electrical signal
92. PLD
94. Counter
96. Counter register
98. Clock

What is claimed is:

1. A method for determining a phase shift in a signal comprising the steps of:
   a) sampling a reference signal for a low going edge;
   b) if a low going edge is detected go to step c), if a low going edge is not detected return to step a);
   c) initializing a counter;
   d) sampling said reference signal;
   e) if a high going edge on said reference signal is detected go to step f), if a high going edge is not detected return to step d);
   f) starting said counter;
   g) sampling a resulting signal;
   h) if said resulting signal is at a high level go to step i), if said resulting level is not at high level go to step o);
   i) sampling said resulting signal;
   j) if a low going edge on said resulting signal is detected go to step k), if not go to step i);
   k) sampling said resulting signal;
   l) if a high going edge on said resulting signal is detected go to step m), if not go to step k);
   m) stopping said counter;
   n) updating a counter register and go to step r);
   o) sampling said resulting signal;
   p) if is a high going edge on said resulting signal is detected go to step q), if not go to step o);
   q) stopping said counter; and
   r) converting said register value to phase difference.

2. A method as in claim 1 wherein the additional following step occurs:
   s) go to step a).

3. A method as in claim 1 wherein a clock is adapted to provide a rate at which said reference signal and said resulting signal are sampled.

4. A method as in claim 1 wherein a clock is adapted to provide a periodic signal which is counted by said counter.

5. A method as in claim 1 wherein a PLD is adapted to perform steps a)–q).

6. A method as in claim 1 wherein said reference signal is a drive signal for an ultrasonic transmitter.

7. A method as in claim 1 wherein said resulting signal is an electrical signal corresponding to a received ultrasonic signal.

8. A method for determining a phase shift in a signal which is transmitted and received, the method comprising:
   starting a counter when a first cross over location from a first-state-to-second-state is detected in the transmitted signal;
   stopping the counter when a second cross over location in the received signal is detected which matches the first-state-to-second-state direction of the first cross over location in the transmitted signal;
   converting a counter value in the counter to a phase difference between the transmitted and received signal
   sampling the transmitted signal;
   detecting a third cross over location from a second-state-to-first-state in the sampled transmitted signal; and
   initializing the counter when the third cross over location is detected.

9. The method as set forth in claim 8 wherein the first state in the transmitted and received signals is at a lower level than the second state in the transmitted and received signals.

10. The method as set forth in claim 8 wherein the second state in the transmitted and received signals is at a lower level than the first state in the transmitted and received signals.

11. The method as set forth in claim 8 wherein the step of stopping the clock further comprises:
    sampling the received signal;
    detecting for the second cross over location in the sampled received signal which matches the first-state-to-second-state direction of the first cross over location, the counter stopping when the second cross over location is detected in the sampled received signal; and
    wherein the sampling of the transmitted signal and the received signal is at a rate set by a clock.

12. A method for determining the presence of multiple documents comprising:
    transmitting a signal through a document feed comprising one or more documents;
    receiving the signal after it has passed through the document feed;
    starting a counter when a first cross over location from a first-state-to-second-state is detected in the transmitted signal;
    stopping the counter when a second cross over location in the received signal is detected which matches the first-state-to-second-state direction of the first cross over location in the transmitted signal;
    converting a counter value in the counter to a phase difference which identifies the number of the documents in the document feed;
    sampling the transmitted signal;
    detecting a third cross over location from a second-state-to-first-state in the sampled transmitted signal; and
    initializing the counter when the third cross over location is detected.

13. The method as set forth in claim 12 wherein the first state in the transmitted and received signals is at a lower level than the second state in the transmitted and received signals.

14. The method as set forth in claim 12 wherein the second state in the transmitted and received signals is at a lower level than the first state in the transmitted and received signals.

15. A method for determining the presence of multiple documents comprising:

transmitting a signal through a document feed comprising one or more documents;

receiving the signal after it has passed through the document feed;

starting a counter when a first cross over location from a first state-to-second state is detected in the transmitted signal;

stopping the counter when a second cross over location in the received signal is detected which matches the first-state-to-second-state direction of the first cross over location in the transmitted signal;

converting a counter value in the counter to a phase difference which identifies the number of the documents in the document feed;

wherein the step of starting the clock further comprises:

sampling the transmitted signal;

detecting for the first cross over location from the first-state-to-second-state in the sampled transmitted signal, the counter starting when the first cross over location is detected in the sampled transmitted signal;

wherein the step of stopping the clock further comprises:

sampling the received signal;

detecting for the second cross over location in the sampled received signal which matches the first-state-to-second-state direction of the first cross over location, the counter stopping when the second cross over location is detected in the sampled received signal; and wherein the sampling of the transmitted signal and the received signal is at a rate set by a clock.

16. A method for determining the presence of multiple documents comprising:

transmitting a signal through a document feed comprising one or more documents;

receiving the signal after it has passed through the document feed;

starting a counter when a first cross over location from a first state-to-second state is detected in the transmitted signal;

stopping the counter when a second cross over location in the received signal is detected which matches the first-state-to-second-state direction of the first cross over location in the transmitted signal;

converting a counter value in the counter to a phase difference which identifies the number of the documents in the document feed; and wherein the signal is an ultrasonic signal.

17. An apparatus for determining a phase shift, the apparatus comprising:

a signaling system which transmits and receives a signal;

a counter;

a detector which starts the counter when a first cross over location from a first-state-to-second-state is detected in the transmitted signal and stops the counter when a second cross over location in the received signal is detected which matches the first-state-to-second-state direction of the first cross over location in the transmitted signal;

a converter which converts a counter value in the counter to a phase difference between the transmitted and the received signals;

wherein the signaling system comprises:

a transmitter for transmitting the signal;

a driver for driving the transmitter; and receiver for receiving the signal.

18. The apparatus as set forth in claim 17 wherein the first state in the transmitted and received signals is at a lower level than the second state in the transmitted and received signals.

19. The apparatus as set forth in claim 17 wherein the second state in the transmitted and received signals is at a lower level than the first state in the transmitted and received signals.

20. An apparatus for determining a phase shift, the apparatus comprising:

a signaling system which transmits and receives a signal;

a counter;

a detector which starts the counter when a first cross over location from a first-state-to-second-state is detected in the transmitted signal and stops the counter when a second cross over location in the received signal is detected which matches the first-state-to-second-state direction of the first cross over location in the transmitted signal;

a converter which converts a counter value in the counter to a phase difference between the transmitted and the received signals; and wherein the signal is an ultrasonic signal.

21. An apparatus for determining a phase shift, the apparatus comprising:

a signaling system which transmits and receives a signal;

a counter;

a detector which starts the counter when a first cross over location from a first-state-to-second-state is detected in the transmitted signal and stops the counter when a second cross over location in the received signal is detected which matches the first-state-to-second-state direction of the first cross over location in the transmitted signal;

a converter which converts a counter value in the counter to a phase difference between the transmitted and the received signals; and a clock which controls a rate at which the detector samples the transmitted signal and the received signal to detect the first cross over location and the second cross over location.

* * * * *